United States Patent [19]

Beisner et al.

[11] 4,225,530
[45] Sep. 30, 1980

[54] RHODIUM CATALYST REGENERATION BY CARBON MONOXIDE TREATMENT

[75] Inventors: Robert W. Beisner, Charleston; Stephen C. Winans, South Charleston, both of W. Va.

[73] Assignee: Union Carbide Corporation, New York, N.Y.

[21] Appl. No.: 968,400

[22] Filed: Dec. 11, 1978

[51] Int. Cl.² ............... C07C 27/06; B01J 31/40; B01J 23/96
[52] U.S. Cl. .................... 260/449 L; 252/411 R; 252/414
[58] Field of Search ............. 252/411 R, 414, 431 N; 260/449 R, 449 L

[56] References Cited

U.S. PATENT DOCUMENTS

| | | | |
|---|---|---|---|
| 3,833,634 | 9/1974 | Pruett et al. | 252/431 N |
| 4,131,640 | 12/1978 | von Kutepow et al. | 252/411 R |

Primary Examiner—P. E. Konopka
Attorney, Agent, or Firm—Bernard Lieberman

[57] ABSTRACT

This invention relates to the continuous production of alkane polyols by the reaction of hydrogen and CO in a homogeneous liquid phase mixture containing a rhodium carbonyl complex catalyst, the mole ratio of $H_2/CO$ in the reactant gas being above about 0.1, wherein the improvement comprises periodically lowering the $H_2/CO$ mole ratio in the reactant gas to about 0.1 or less and thereafter increasing the $H_2/CO$ mole ratio to about its former value.

3 Claims, 1 Drawing Figure

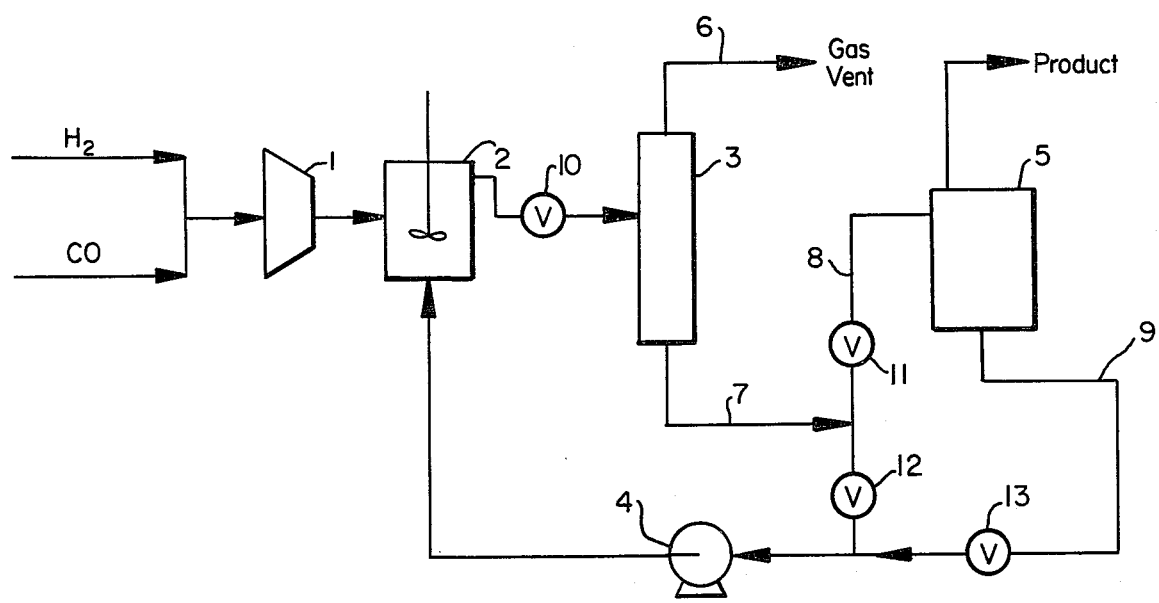

RHODIUM CATALYST REGENERATION BY CARBON MONOXIDE TREATMENT

This invention is concerned with a process for improving the production of alkane polyols, as well as a variety of other chemicals, in particular, methanol, from the reaction of synthesis gas in a homogeneous liquid phase mixture containing a rhodium carbonyl complex catalyst.

There are described in U.S. Pat. No. 3,833,634 issued Sept. 3, 1974, and U.S. Pat. No. 3,957,857 issued May 18, 1976, processes for reacting hydrogen and oxides of carbon in the presence of rhodium carbonyl complex catalysts. The conditions employed in those processes involve reacting a mixture of an oxide of carbon and hydrogen with a catalytic amount of rhodium in complex combination with carbon monoxide, at a temperature of between about 100° C. to about 375° C. and a pressure of between about 500 psia to about 50,000 psia.

In addition to the aforementioned U.S. Patents, the following U.S. Patents amplify the development of the processes for making alkane polyols from gaseous mixtures containing hydrogen and carbon monoxide in the presence or a rhodium carbonyl complex catalyst.

| U.S. Pat. No. 3,878,292 | Patented April 15, 1975 |
| --- | --- |
| U.S. Pat. No. 3,878,290 | Patented April 15, 1975 |
| U.S. Pat. No. 3,878,214 | Patented April 15, 1975 |
| U.S. Pat. No. 3,886,364 | Patented May 27, 1975 |
| U.S. Pat. No. 3,940,432 | Patented February 24, 1976 |
| U.S. Pat. No. 3,929,969 | Patented December 30, 1975 |
| U.S. Pat. No. 3,952,039 | Patented April 20, 1976 |
| U.S. pat. No. 3,948,965 | Patented April 6, 1976 |
| U.S. Pat. No. 3,944,588 | Patented March 16, 1976 |
| U.S. Pat. No. 3,957,857 | Patented May 18, 1976 |
| U.S. Pat. No. 3,968,136 | Patented July 6, 1976 |
| U.S. Pat. No. 3,974,259 | Patented August 10, 1976 |
| (formerly U.S. Ser. No. 455,380, filed March 27, 1974) | |
| U.S. Pat. No. 3,989,799 | Patented November 2, 1976 |
| (formerly U.S. Ser. No. 455,379, filed March 27, 1974) | |
| U.S. Pat. No. 4,013,700 | Patented March 22, 1977 |
| (formerly U.S. Ser. No. 526,942, filed November 25, 1974) | |
| U.S. Ser. No. 488,139 (now abandoned) | Filed July 12, 1974 |
| U.S. Ser. No. 506,862 (now abandoned) | Filed September 17, 1974 |
| U.S. Pat. No. 4,001,289 | Patented January 4, 1977 |
| (formerly U.S. Ser. No. 506,864, filed September 17, 1974) | |
| U.S. Ser. No. 506,865 (now abandoned) | Filed September 17, 1974 |
| U.S. Ser. No. 615,093 (now abandoned) | Filed September 19, 1975 |
| U.S. Ser. No. 537,885 (now abandoned) | Filed January 2, 1975 |
| U.S. Ser. No. 618,023 (now abandoned) | Filed September 30, 1975 |
| U.S. Ser. No. 618,061 (now abandoned) | Filed September 30, 1975 |
| U.S. Ser. No. 618,021 | Filed September 30, 1975 |
| U.S. Ser. No. 727,646 (now abandoned) | Filed September 29, 1976 |
| U.S. Ser. No. 782,986 | Filed March 30, 1977 |
| (now U.S. Pat. No. 4,111,975, patented September 5, 1978). | |

The processes described in the foregoing patents are conducted in a homogeneous liquid phase, which means that the catalyst, the reaction products and the promoter, if present, are in a solution. The solution typically requires the presence of a solvent, primarily to keep the rhodium catalyst in solution. However, rhodium carbonyl complexes vary in structure depending upon many variables, such as, temperature, solvent, promoter, and the carbon monoxide and hydrogen pressure employed, such that a complex which may be extremely stable in solution at one set of operating conditions could precipitate out of solution, for example, at a different pressure, or temperature, or in the presence of a different promoter or solvent. In addition, it has been observed that even at seemingly constant operating conditions, rhodium catalyst is continuously lost from solution during periods of extended operation resulting in reduced productivity of reaction product. Consequently, it was heretofore necessary to periodically add soluble rhodium compounds to form new catalyst in order to maintain the desired level of reaction productivity.

In large-scale industrial processes, catalyst losses are generally unacceptable, particularly when the catalyst contains rhodium metal which is currently priced at about $500 per troy ounce. Thus, for example, in the processes described in the aforementioned patents, it is estimated that rhodium losses on the order of about 0.1% by weight on a per pass basis would be sufficient to make the process uneconomical. Accordingly, the commercialization of these processes necessitates that the loss of rhodium metal be kept well below 0.1%, by weight, if the cost of the reaction product is not to exceed the cost of such products when manufactured by other competitive processes.

There is described herein an improved process for continuously forming alkane polyols at high levels of productivity from the reaction of hydrogen and CO in a homogeneous liquid mixture containing a rhodium carbonyl complex catalyst, the mole ratio of $H_2/CO$ in the reactant gas being above about 0.1, wherein the $H_2/CO$ mole ratio in the reactant gas is periodically lowered to 0.1 or less and thereafter raised to about its former value.

It has been found that the reaction productivity which generally declines over extended periods of time during normal operation, can be restored to about its original level by lowering the normal $H_2/CO$ mole ratio in the gaseous reactants provided to the homogeneous liquid phase, generally substantially above 0.1, to about 0.1 or less for a period of time sufficient to at least partially convert the rhodium to a more active catalytic state and thereafter increasing the $H_2/CO$ mole ratio to about its former value. The loss of reaction productivity which occurs during extended periods of operation is believed to be due to conversion of rhodium to an inactive form, for example, precipitation of rhodium from the catalyst solution. Experimental evidence indicates that rhodium which is lost or precipitated from solution is resolubilized during such period of time that the $H_2/CO$ mole ratio in the reactant gas is temporarily lowered in accordance with the invention thereby resulting in an increased level of productivity when the reaction is conducted, once again, at the former $H_2/CO$ mole ratio in the reactant gas.

The relative molar amounts of hydrogen and carbon monoxide which are initially present in the reaction mixture is generally varied from about 10:1 to above about 1:10, and preferably from about 5:1 to about 1:5. For purposes of increasing reaction productivity in accordance with the invention, a feed gas comprised solely of carbon monoxide is preferred although any $H_2/CO$ mole ratio below 0.1 may be suitably employed.

Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, mixtures containing carbon dioxide and hydrogen or mixtures of carbon dioxide, carbon monoxide and hydrogen can also be employed. If desired, the mixture can comprise steam and carbon monoxide.

The amount of time required to effect resolubilization of rhodium precipitated from solution at the lowered $H_2/CO$ mole ratio will generally vary from the order of about several minutes to about 40 hours depending upon numerous variables, such as, temperature and pressure of the reaction mixture, product concentration and the hydrogen to carbon monoxide mole ratio. For example, the higher the temperature, the longer the time period required to effect resolubilization of precipitated rhodium, while the higher the pressure and the lower the $H_2/CO$ mole ratio, the shorter the corresponding time period necessary to effect such rhodium resolubilization.

There is described in commonly assigned copending application Ser. No. 786,584, filed Apr. 11, 1977, a process for separating products from a rhodium-containing solution wherein catalyst instability is minimized by contacting the solution with carbon monoxide. Unlike the present invention, the process therein described is not concerned with reaction productivity, but rather, with preventing rhodium instability when separating the alcohol products from the rhodium-containing reaction mixture. The present invention, on the other hand, seeks to restore a declining reaction productivity to approximately its original level by what is believed to be either resolubilization of rhodium precipitated from solution or reactivation to a more active catalytic form.

The rhodium carbonyl complex catalysts suitable for use herein may be in the form of rhodium carbonyl clusters. P. Chini, in a review article entitled "The Closed Metal Carbonyl Clusters" published in Review (1968), Inorganica Chimica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster". The rhodium carbonyl cluster compounds contain rhodium bonded to rhodium or rhodium bonded to another metal, such as cobalt, and/or iridium.

The preferred rhodium carbonyl cluster compounds are those which contain rhodium-rhodium bonds. These compounds desirably contain carbon and oxygen in the form of carbonyl (—CO), in which the carbonyl may be "terminal", "edge-bridging", and/or "face-bridging". They may also contain hydrogen and carbon in forms other than carbonyl.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chimica Acta, 3:2 pp 299–302, June (1969). Of particular analytical utility in the present invention is the use of infrared spectroscopy which allows for characterization of the particular rhodium carbonyl complex present during the operation of the process of the present invention.

The precise role of the rhodium carbonyl complexes, such as the rhodium carbonyl clusters, in the reaction of hydrogen with oxides of carbon to produce polyhydric alcohols is not fully appreciated at present. Under the reaction conditions of the present process the carbonyl complexes are believed to be anionic in their active forms.

Infrared spectra under reaction conditions of the present process have shown $Rh(CO)_4^-$, $RH_{13}(CO)_{24}H_3^{-2}$, $Rh_6(CO)_{15}H^-$, $RH_{13}(CO)_{24}H_2^{-3}$, and $[Rh_{12}(CO)_{34-36}]^{2-}$ anions, and other rhodium clusters to be present at various concentrations at different times of the reaction. These may represent the active rhodium carbonyl species responsible for polyhydric alcohol formation or may be merely symptomatic of some further intermediate transitory rhodium carbonyl structure which serves to convert the carbon monoxide and hydrogen to the polyhydric alcohol.

A number of nitrogen and/or oxygen-containing bases may also be used in the process of the present invention. For the purposes of this invention, the bases can be considered to promote the activity of the rhodium catalyst.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the

group and the "oxy" oxygen in the

group that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic azo-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacet acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine N-(2-hydroxyethyl) iminodiacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di-, tri-, tetraamines, etc.) and those compounds in which the Lewis base nitrogen forms part of a ring structure as in pyridine, quinoline, pyrimidine morpholine, hexamethylenetetraamine, and the like. In addition any compounds capable of yielding an amino nitrogen under the reaction conditions of the present invention are promoters, as in the case of an amide, such as formamide, cyanamide, and urea, or an oxime. Further illustrative of Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino) pyridine; quinoline; substituted quinolines, such as 2-(dimethylamino)-6-methoxyquinoline; 4,5-phenanthroline; 1,8-phenanthroline; 1,5-phenanthroline; piperazine; substitute piperazines such as N-methylpiperazine, N-ethylpiperazine, 2-methyl-N-methylpiperazine; 2,2'dipyridyl; methyl-substituted 2,2-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo[2.2.2]octane, purine and the like.

Also included herein are the use of dimorpholine compounds characterized by the formula:

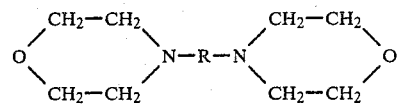

wherein R is divalent alkylene of 1 to about 30 carbon atoms and 1.4-phenylene.

Under reaction conditions the promoter is preferably used in amounts from about 0.02 to about 40 equivalents of promoter, most preferably from about 0.1 to about 20 equivalents promoter, for every atom of rhodium in the reaction mixture. The number of equivalents of promoter is equal to the number of molecules of promoter times the number of nitrogen atoms in each molecule.

The process of this invention can also be carried out by providing salts in the homogeneous liquid phase reaction mixture. Suitable salts include any organic or inorganic salt which does not adversely affect the production of polyhydric alcohols. Experimental work suggest that many salts are beneficial as either a copromoter and/or in aiding in maintaining rhodium in solution during the reaction. Illustrative of useful salt promoters are the ammonium salts and the salts of the metals of Group I and Group II of the Periodic Table (Handbook of Chemistry and Physics—50th Edition) for instance the halide, hydroxide, alkoxide, phenoxide and carboxylate salts such as sodium fluoride, cesium fluoride, cesium pyridinolate, cesium formate, cesium acetate, cesium benzoate, cesium p-methylsulfonyl-benzoate ($CH_3SO_2C_6H_4COO$)Cs, rubidium acetate, magnesium acetate, strontium acetate, ammonium formate, ammonium benzoate and the like. The cesium, rubidium, potassium and ammonium salts are preferred.

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In addition, the anion of the above salt may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; $[Rh_{12}(CO)_{30}]^{2-}$; $Rh_{13}(CO)_{24}H_3^{-2}$; and $Rh_{13}(CO)_{24}H_2^{-3}$.

Under reaction conditions where a salt is employed the salt is desirably added with the initial charge of reactants in amounts of from about 0.5 to about 2.0 gram moles, preferably from about 0.8 to about 1.6 moles, and most preferably from about 0.9 to 1.4 moles of salt for every five gram atoms of rhodium present in the reaction mixture.

Illustrative solvents which are generally suitable in making the homogeneous mixture include, for example, ethers such as tetrahydrofuran, tetrahydropyran, diethyl ether, 1,2-dimethoxybenzene, 1,2-diethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxyethylenepropylene glycol, etc; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; gamma-butyrolactone, deltavalerolactone; substituted and unsubstituted tetrahydrothiophene-1,1-dioxides (sulfolanes) as disclosed in U.S. application No. 537,885, filed on Jan. 2, 1975, the disclosure at pages 6 and 7 of the specification of which is incorporated herein by reference.

Also, the crown ethers are suitable herein, particularly those as described in U.S. patent application Ser. No. 832,384 filed Sept. 13, 1977, which application is incorporated herein by reference and is now U.S. Pat. No. 4,162,261, issued July 24, 1979. The crown ethers described therein contain at least four oxygen heteroatoms and include [18]-crown-6 and [15]-crown-5.

Particularly desirable solvents are tetraglyme, sulfolane, gamma-butyrolactone and the crown ethers. Other very desirable solvents include mixtures of tetraglyme and sulfolane, mixtures of sulfolane and butyrolactone, mixtures of crown ethers and sulfolane, mixtures of crown ethers and tetraglyme, mixtures of crown ethers and butyrolactone, mixtures of tetraglyme and butyrolactone.

In practicing the method of the present invention, the synthesis of the desired alkane diols and derivatives thereof, by the reaction of hydrogen with an oxide of carbon is suitably conducted under operative conditions, as heretofore described, which give reasonable reaction rates and/or conversions.

The process is suitably effected over a wide superatmospheric pressure range of from about 500 psia to about 50,000 psia. Pressures as high as 50,000 psia, and higher can be employed but with no apparent advantages attendant thereto which offset the unattractive plant investment outlay required for such high pressure equipment. Therefore, the upper pressure limitation is desirably approximately 16,000 psia. Effecting the present process below about 16,000 psia, especially below about 13,000 psia, and preferably at pressures below about 8000 psia, results in cost advantages which are associated with low pressure equipment requirements. In attempting to foresee a commercial operation of this process, pressures between about 4,000 psia and 16,000 psia appear to represent most realistic values.

In a preferred embodiment of the present invention the pressures referred to above represent the total pressures of hydrogen and oxides of carbon in the reactor.

The temperature which may be employed can vary over a wide range of elevated temperatures. In general, the process can be conducted at a temperature in the range of from about 100° C. and upwards to approximately 375° C., and higher. Temperatures outside this stated range are not excluded from the scope of the invention. At the lower end of the temperature range, and lower, the rate of reaction to desired product becomes markedly slow. At the upper temperature range, and beyond, signs of some catalyst instability are noted. Notwithstanding this factor, reaction continues and alkane polyols and/or their derivatives are produced. Additionally, one should take notice of the equilibrium reaction for forming ethylene glycol:

$$2CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher pressures, however, do not represent preferred embodiments of the invention in view of the high investment costs associated with erecting chemical plants which utilize high pressure utilities and the necessity of fabricating equipment capable of withstanding such enormous pressures. Suitable temperatures are between about 150° C. to about 320° C., and desirably from about 210° C. to about 300° C.

The novel process is effected for a period of time sufficient to produce the alkane polyols and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressures exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The active forms of the rhodium carbonyl clusters may be prepared by various techniques. They can be preformed and then introduced into the reaction zone. Alternatively, any of the host of rhodium-containing substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium(II) propionate, rhodium(II) butyrate, rhodium(II) valerate, rhodium(III) naphthenate, rhodium dicarbonyl acetylacetonate, rhodium tri(acetylacetonate), rhodium trihydroxide, indenylrhodium dicarbonyl, rhodium dicarbonyl (1-phenylbutane-1,3-dione), tris(-hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), triacontacarbonyl rhodium salts and rhodium-containing compounds deposited on porous supports or carriers capable of providing rhodium carbonyls in solution, and others.

The preparation of the rhodium carbonyl complex compounds can be conveniently carried out in the solvent mixture. Tetrarhodium dodecacarbonyl, though of limited solubility, can be added to the solvent in a finely divided form. Any of several of the rhodium-containing compounds illustrated previously can be employed in lieu of tetrarhodium dodecacarbonyl. The rhodium carbonyl complex or cluster forming reaction can be effected under a carbon monoxide pressure, with or without $H_2$, of about 1 to 15 atmospheres, and higher, using a temperature of about 30° C. to about 100° C., for a period of time ranging from minutes to a few days, generally from about 30 minutes to about 24 hours. The resulting rhodium carbonyl complex contained in the solvent mixture is catalytically active in this process.

In order to illustrate the invention reference is made to the drawing which shows a schematic flowsheet describing a liquid recycle system for the continuous operation of the process of the invention.

Reactor 2 is a heat jacketed stainless steel autoclave capable of withstanding reaction pressures of up to 2,000 atmospheres. Provided in reactor 2 is the liquid phase mixture containing the rhodium carbonyl complex catalyst dissolved therein. Hydrogen and carbon monoxide are mixed in the desired molar ratio using a metering system (not shown) which allows the composition of the exit gas to vary from pure $H_2$ to pure CO. The resultant gas feed is passed through gas compressor 1 and fed to reactor 2 in quantities sufficient to saturate the liquid phase mixture in the reactor but less than an amount whereby a discrete gas phase will form in the reaction zone. Reactor 2 is provided with an agitator to uniformly distribute the $H_2$/CO gas mixture in the liquid body thus providing intimate gas-liquid contact.

In operating reactor 2 in an overflow (or liquid full) configuration, the liquid phase mixture comprising the catalyst solution, reaction products and dissolved reactant gas is withdrawn from the top of reactor 2 and is passed through pressure reducing valve 10 to a liquid-vapor separator 3 where a portion of the unconverted reactant gas dissolved in the liquid mixture comes out of solution at the reduced pressure of the separator and is vented through line 6. The liquid mixture leaving separator 3 is either returned directly to reactor 2 via line 7, pressure reducing valve 12 and liquid pump 4, or alternatively, sent through line 8, and pressure reducing valve 11 to CO stripper 5 for recovery of product, predominantly ethylene glycol with varying amounts of polyols such as glycerine, propylene glycol and methanol. Stripper 5 is a vertical packed column filled with a high surface area packing, the liquid feed entering near the top being stripped by a counter-current flow of carbon monoxide or optionally a CO/$H_2$ mixture which is then further processed for product recovery. The liquid mixture exiting at the bottom of stripper 5 is recycled to reactor 2 through line 9, valve 13 and pump 4. Valve 13 prevents the flow of liquid mixture leaving valve 12 from entering stripper 5; valve 13 being closed when the liquid mixture in line 7 bypasses stripper 5.

As an alternative to operating reactor 2 in an overflow configuration, as described above, reactor 2 may operate as a vapor-stripping reactor in a gas recycle system. In this mode of operation, the liquid level of catalyst solution in reactor 2 is controlled such that a liquid-vapor interface is maintained in the reactor, the vapor space above the liquid phase mixture being composed of excess reactant gas and reaction product. An excess amount of $H_2$ and CO reactant gas mixture is thus introduced into the bottom of reactor 2 to contact the catalyst solution therein and strip therefrom vaporous products of the reaction and solvent. The CO/$H_2$ gas mixture in the vapor space is thus saturated with vaporous reaction products and solvent vapors and passes from the top of reactor 2 into vapor-liquid separator 3. For a gas recycle system, the operating pressure of separator 3 is preferably maintained at the pressure of reactor 2. A heat exchanger may be provided wherein all but the CO/$H_2$ mixture is liquified and recovered from line 7, the CO/$H_2$ mixture being withdrawn through line 6 and recycled to reactor 2 (gas recycle not shown in drawing). The consensed liquid mixture in line 7 is then sent to stripper 5, as previously described, for recovery of product, the remaining liquid in stripper 5 exiting through line 9 for recycle to reactor 2.

To further illustrate the invention, the following examples were operated in accordance with the liquid recycle system depicted in FIG. 1. Reactor 2 was operated in a liquid-full configuration. In the specific practice of the examples, a 30 or 60 pound charge of solution, as the case may be, containing solvent, rhodium dicarbonyl acetylacetonate, and promoters was initially introduced into a holding tank (not shown in the drawing) under nitrogen pressure. A 1:1 mole mixture of $H_2$/CO, at the desired gas feed rate, was introduced into a 1.5 or 6 liter capacity stainless steel reactor (depending upon the particular example) until the desired reactor pressure was established in the system. The catalyst solution was then charged from the holding tank into the reactor and the reactor then heated to the desired reaction temperature.

The dimensions of the 1.5 and 6 liter reactors used in the examples were as follows: $3\frac{5}{8}''$ I.D.$\times 9''$ and $5\frac{1}{2}''$ I.D.$\times 18''$. The liquid-vapor separator was a 2 liter capacity stainless steel vessel, 3" I.D., 18" long. The CO stripper was a 2" I.D. tube, 8 ft. long.

The separator was operated at about 2,000 psig and the pressure of the CO stripper was about 15 psig.

EXAMPLE I

A 60 lb. charge of catalyst solution containing 750 ppm by weight rhodium (added as rhodium dicarbonyl acetylacetonate) and having a 6 to 1 molar ratio of rhodium to cesium (180 ppm cesium added as cesium 2-hydroxypyridinate) and a 4 to 1 molar ratio of 2-hydroxypyridine to rhodium in tetraglyme solvent was introduced into a liquid recycle system, as described above, having a 6 liter stainless steel reactor. The gas feed was a 1:1 molar mixture of $H_2$/CO, the reaction temperature was 220° C. and the reaction pressure was 10,000 psig. After 60 hours of operation, the rhodium concentration in solution declined to about 425 ppm and the cesium concentration to about 115 ppm. The $H_2$ feed was then discontinued so that the feed gas was comprised solely of carbon monoxide, the other reaction variables remaining unchanged. After 24 hours at these conditions, the rhodium concentration in solution increased to about 710 ppm and the cesium concentration increased to about 172 ppm.

EXAMPLE II

A 30 lb. charge of catalyst solution containing about 5700 ppm by weight rhodium (added as rhodium dicarbonyl acetylacetonate), about 1.5 weight percent N-methylmorpholine and having a 3 to 1 molar ratio of rhodium to potassium (charged as potassium benzoate) in 18-Crown-6 solvent was introduced into a liquid recycle system having a 1.5 liter reactor. The gas feed was a 1:1 mole ratio of $H_2$/CO, the reactor temperature was 250° C., the reactor pressure was 15,000 psig, and the productivity of ethylene glycol was about 2.3 gram-moles per hour. After 70 hours of operation, the rhodium concentration in solution declined to about 4000 ppm and the productivity declined to about 1.5 g-moles per hour. The hydrogen feed was discontinued so that the feed gas was comprised solely of CO. After 8 hours at these conditions the rhodium concentration in solution had increased to about 5500 ppm. Upon restarting the $H_2$ feed so that the feed gas was, once again, a 1:1 mole ratio of $H_2/CO$, the glycol productivity was about 2.2 g-moles/hour.

What is claimed is:

1. In a process for continuously producing alkane polyols by the reaction of hydrogen and carbon monoxide in a homogeneous liquid phase mixture containing a rhodium carbonyl complex catalyst, the mole ratio of $H_2/CO$ in the reactant gas being above about 0.1, the improvement which comprises periodically lowering the $H_2/CO$ mole ratio in the reactant gas to about 0.1 or less and thereafter increasing the $H_2/CO$ mole ratio to about its former value.

2. The process of claim 1 wherein in said improvement the $H_2/CO$ mole ratio in the reactant gas is lowered sufficiently below 0.1 such that the gas consists essentially of carbon monoxide.

3. The process of claim 1 wherein the reaction temperature of hydrogen and carbon monoxide in the liquid phase mixture is from about 100° C. to about 375° C.

* * * * *